United States Patent [19]

Felix et al.

[11] Patent Number: 5,565,393
[45] Date of Patent: Oct. 15, 1996

[54] CORROSION RESISTANT EQUIPMENT FOR MANUFACTURING HIGHLY FLUORINATED ALKANES

[75] Inventors: Vinci M. Felix, Kennett Square, Pa.; Richard E. Fernandez, Bear; Charles C. Seastrom, New Castle, both of Del.

[73] Assignee: E. I. Du Pont de Nemours and Company, Wilmington, Del.

[21] Appl. No.: 312,484

[22] Filed: Sep. 26, 1994

Related U.S. Application Data

[63] Continuation of Ser. No. 949,313, Sep. 22, 1992, abandoned.

[51] Int. Cl.$^6$ .................................................. B01J 38/00
[52] U.S. Cl. ........................ 502/20; 502/32; 502/224; 502/228; 422/241; 570/168
[58] Field of Search ...................... 502/32, 228, 224; 422/241

[56] References Cited

U.S. PATENT DOCUMENTS

| | | | |
|---|---|---|---|
| 2,268,983 | 1/1942 | Gilmore et al. | 82/1 |
| 2,768,983 | 10/1956 | Couper et al. | 260/668 |
| 3,205,574 | 9/1965 | Brennecke | 29/494 |
| 3,233,312 | 2/1966 | Cowan et al. | 29/194 |
| 3,264,731 | 8/1966 | Chudzik | 29/486 |
| 3,375,109 | 3/1968 | Peters | 75/212 |
| 3,397,045 | 8/1968 | Winter | 29/191 |
| 3,397,444 | 8/1968 | Bergmann et al. | 29/470.1 |
| 3,474,344 | 10/1969 | Perl | 220/3 |
| 3,493,353 | 2/1970 | Bergmann et al. | 29/191 |
| 3,554,126 | 1/1971 | Bergmann et al. | 102/24 |
| 4,258,225 | 3/1981 | Feiring | 570/168 |
| 4,967,024 | 10/1990 | Gumprecht et al. | 570/168 |
| 5,057,286 | 10/1991 | Chiba et al. | 422/245 |
| 5,226,579 | 7/1993 | Bergmann et al. | 228/107 |
| 5,323,955 | 6/1994 | Bergmann et al. | 228/262.7 |
| 5,400,945 | 3/1995 | Bergmann et al. | 228/107 |

FOREIGN PATENT DOCUMENTS

| | | |
|---|---|---|
| 1117095 | 11/1961 | Germany . |
| WO91/05752 | 5/1991 | WIPO . |

OTHER PUBLICATIONS

*Superacids*, A Wiley–Interscience Publication, Jun. 16, 1989, pp. 1–10—George A. Olah et al.
Properties of Precious Metals, Silver and Silver Alloys, by E. M. Wise and C. D. Coxe, pp. 1181–1195 (1961).

*Primary Examiner*—Anthony McFarlane
*Attorney, Agent, or Firm*—Michael K. Boyer

[57] ABSTRACT

Process is disclosed for preparing a highly fluorinated alkane by contacting halogenated alkenes or alkanes with hydrogen fluoride in the presence of a catalyst which produces a super acid environment. Also, performing the fluorination process by using equipment having a corrosion resistant surface. The corrosion resistant surface may be provided by explosively cladding a corrosion resistant material onto a base metal.

7 Claims, 1 Drawing Sheet

CORROSION RESISTANT EQUIPMENT FOR MANUFACTURING HIGHLY FLUORINATED ALKANES

This is a continuation of application Ser. No. 07/949,313, filed Sep. 22, 1992, now abandoned.

FIELD OF THE INVENTION

The present invention relates to corrosion-resistant materials which are used for fabricating equipment that is exposed to a process for manufacturing highly fluorinated alkanes.

BACKGROUND OF THE INVENTION

For many years various chlorofluorinated carbons such as trichlorofluoromethane (CFC-11), dichlorodifluoromethane (CFC-12) chlorodifluoromethane (HCFC-22), and 1,1,2-trichlorotrifluoroethane (CFC-113) have been used in applications such as refrigerating, air conditioning, cleaning, and blowing agents. The manufacture of these chlorinated compounds have been regulated with the aim of phasing them out completely as a result of their potential damaging affects to the ozone layer. The search for replacements has led to the development of a number of alternative compounds. One such alternative compound is 2,2-dichloro-1,1,1-trifluoroethane, generally referred to as HCFC-123. Other potentially important alternative compounds such as 2-chloro-1,1,1,2-tetrafluoroethane (HCFC-124), pentafluoroethane (HFC-125), among others, may be produced by using HCFC-123 as a starting material.

The conventional processes for manufacturing the alternative compounds involve reacting an alkane or alkene with hydrogen fluoride while in the presence of a catalyst. The equipment which is used for handling or manufacturing the alternative compounds is exposed to a highly corrosive, and typically erosive environment which consumes or degrades conventional processing equipment. The corroding equipment releases corrosion by-products or contaminates into the manufacturing process and resultant product. These contaminants reduce reaction rates, become involved in unintended reactions, inhibit catalytic activity, etc.

Moreover, conventional equipment which is in the form of a loosely lined autoclave or pressure vessel lacks an adequate thermal conductivity, e.g., a lined autoclave contains a stationary vapor space between the interior and exterior walls.

SUMMARY OF THE INVENTION

The present invention relates to corrosion resistant materials which are used for fabricating equipment that is exposed to a process for manufacturing highly fluorinated alkanes. The corrosion resistant equipment is used for manufacturing fluorinated alkanes by reacting halogenated alkenes or alkanes and HF while in the presence of a catalyst which comprises at least one of $TaF_5$, $NbF_5$, $SbF_5$, $MoF_5$, $AsF_5$, among others. For example, equipment such as reaction vessels, pipes, valves, among others, may be fabricated from clad base metals such that the surface of the equipment which is exposed to the reaction comprises a corrosion resistant material. Suitable corrosion resistance metals comprise at least one of gold, palladium, platinum, molybdenum, rhenium, tungsten, eutectic alloys of molybdenum/rhenium, molybdenum/rhenium/tungsten, tungsten/rhenium, gold/copper, gold/nickel, among others.

The corrosion resistant metal must be capable of withstanding exposure to a super acid environment which has $H_o$ that ranges from about −10 through at least about −30. For best results, corrosion resistant metal and the base metal are explosively bonded together such that the thermal conductivity of the resultant composite is sufficient to permit heating the reaction vessel by an external means.

DETAILED DESCRIPTION OF THE INVENTION

Figure 1:
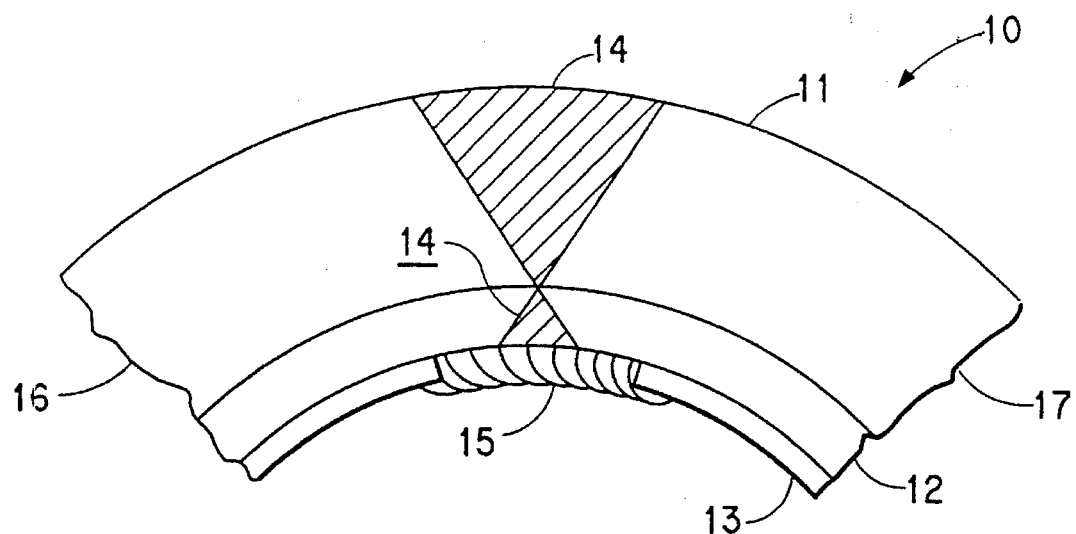
FIG. 1—FIG. 1 is a schematic of a cross-section of a wall of a chemical reactor formed according to the invention.

The present invention relates to obtaining corrosion resistant composites which are used for fabricating equipment which is exposed to a super acid process for producing highly fluorinated alkanes. The fluorinated alkanes are produced by reacting halogenated alkenes or alkanes with HF while in the presence of any suitable trivalent, tetravalent, and/or pentavalent metal halide such as at least one catalyst from the group of $TaF_5$, $NbF_5$, $SbF_5$, $MoF_5$, $AsF_5$, among others. Suitable techniques for manufacturing the fluorinated alkanes can be liquid or vapor phase reactions such as disclosed in U.S. Pat. Nos. 4,258,225 and 4,967,024; the disclosure of which is hereby incorporated by reference.

Equipment such as agitators, reaction vessels, pipes, tubes, valves, among others, which are exposed to the fluorination reaction are fabricated from clad metals or composites such that the surface of the equipment contacted by or exposed to the process comprises a corrosion resistant metal. In some cases, the equipment may comprise a continuous length of a pipe or tube which was fabricated from a corrosion resistant metal. The clad metal may be obtained by explosively cladding a corrosion resistant material onto a base metal, thereby obtaining a composite. One or more composites may be welded, brazed, among others, together in order to obtain the equipment for producing the halogenated alkanes. For example, a single composite may be rolled or bent, and then welded to obtain an open-ended cylinder.

Suitable corrosion resistant metals comprise at least one of gold, palladium, platinum, molybdenum, rhenium, tungsten, or alloys of molybdenum/rhenium, molybdenum/rhenium/tungsten, tungsten/rhenium, gold/copper or gold/nickel, among others.

The corrosion resistant equipment which is produced in accordance with the invention substantially reduces, if not eliminates, the quantity of corrosion by-products or contaminates which are released into the fluorination process, e.g., conventional equipment degraded thereby releasing undesirable by-products into the process. These contaminates can reduce reaction rates, become involved in unintended reactions, inhibit catalytic activity, e.g., deactivation or poisoning of the catalyst, and taint the finished product. As a result, the invention solves the problems associated with conventional equipment and advantageously permits manufacturing high-quality fluorinated alkanes in a super acid environment which minimizes equipment replacement and contamination of the fluorination process.

Whenever used in the specification and appended claims the terms below are intended to have the following definitions.

"Super acid" is intended to refer to the environment within a reaction vessel which can be formed by an interaction of a catalyst, e.g., $TaF_5$, $NbF_5$, $SbF_5$, among others, and hydrogen fluoride. Super acid is quantified in terms of $H_o$ which is defined as:

$$H_o = pK_{BH+} - \log^{[BH+]}/_{[B]}.$$

wherein B is an electro-neutral weak base such as p-nitrotoluene, among others and H is hydrogen. In the present invention, the $H_o$ can range from about −10 to at least about −30.

"Metal" is intended to refer to both pure metals and metal alloys.

"Composite" is intended to refer to a plurality of layers of the same or chemically different metals which have been metallurgically bonded, i.e., substantially without diffusion, together by explosively bonding/cladding to form an integral structure. The integral structure comprises at least two layers, namely, a corrosion resistant layer and a base layer. A composite which possesses an acceptable corrosion resistance and thermal conductivity is obtained by appropriately selecting metal layers which are explosively bonded together.

In some cases an intermediate layer is located between, and is in intimate contact with the corrosion resistant metal and base metal layers. A suitable intermediate layer may comprise at least one member from the group of copper, silver, tantalum, Hastelloy B-series alloys, Hastelloy C-series alloys, among others. The thickness of the intermediate layer typically ranges from about 0.010 to about 0.250 inch. For example, one or more copper intermediate layers may be used for dissipating any heat which is generated when two or more composites are joined together, e.g., by welding, brazing, among others. Further, the intermediate layer may serve to enhance or modify the thermal conductivity of the composite, e.g., providing an intermediate layer comprising Hastelloy C-276 typically decreases the thermal conductivity of the composite in comparison to an intermediate layer comprising copper or silver. The intermediate layer may also serve as an additional corrosion barrier.

"Corrosion resistant" is intended to refer generally to super acid corrosion resistance, but may also include abrasion/erosion resistance. An acceptable corrosion rate is less than about 1.0 mil/year (thousands of an inch per year).

"Base metal" is intended to refer to metals on which the corrosion resistant metal is explosively clad in order to form a composite. Examples of suitable base metals comprise at least one of carbon steel, stainless steel, aluminum, among others. The base metal functions to enhance the structural integrity of the composite. In the case of one-sided composites, normally the base metal is the backer or base layer onto which the corrosion resistant metal is explosively clad. For two-sided composites, opposing faces of the base or backer layer are clad with the same or chemically different metals. Typically, the base metal has a thickness which ranges from about 0.375 inch up to the thickness required to withstand the pressure induced stresses within a vessel.

"Reaction vessel", "vessel", or "manufacturing equipment", is intended to refer to any article of manufacture which is fabricated from one or more composites. Composites may be used for fabricating any equipment which can withstand the super acid fluorination environment. The design or configuration of the reactor, vessel, among others, does not form a critical aspect of the invention so long as the cross-section or wall of the equipment has an acceptable structural integrity and thermal conductivity.

"Explosion or explosively bonded", is intended to refer to a process for fabricating a composite. An explosive is detonated which propels at least one of the layers to be bonded towards the other layer. Any suitable explosion bonding technique may be used in accordance with this invention to form a composite. Examples of suitable explosion bonding techniques are discussed in U.S. Pat. Nos. 3,397,444, 3,493,353, 3,554,126, 3,205,574, 3,233,312, 3,264,731, and commonly assigned and copending patent application Ser. No. 07/876,606, all of which are hereby incorporated by reference. As a result of using explosion bonding, the corrosion resistant and base metals layers are intimately bonded together which produces a composite that is resistant to super acid conditions and has a relatively high thermal conductivity.

At least one composite is fabricated into a vessel that is employed for manufacturing fluorinated alkanes having a formula corresponding to:

R1R2R3C—CR4R5R6 wherein R1, R2, R3, R4, R5 and R6 are individually selected from H, F and Cl, wherein at least one of R1, R2 and R3 is H, and at least one of R4, R5 and R6 is F. In some cases, R4 may comprise at least one of a halogenated or partially halogenated methyl, ethyl or propyl group. The fluorinated alkane may be formed by contacting, at a temperature from about 0° C. to about 175° C. under substantially anhydrous conditions, one molar equivalent of a halogenated alkene of the formula:

R1R2C=CR3R4 wherein R1, R2, R3 and R4 are individually selected from H, F and Cl, with at least the stoichiometric molar equivalent of HF in the presence of at least about 0.25 molar equivalent of at least one catalyst selected from tantalum pentafluoride ($TaF_5$) and niobium pentafluoride ($NbF_5$), antimony pentafluoride ($SbF_5$), among others, preferably with the proviso that the number of moles, x, of catalyst plus the number of moles, y, of HF, relative to the number of moles, z, of the halogenated starting material, are such that the total fluorine-to-starting material ratio, (5x+y)/z, equals at least (6-w), preferably (10-w) wherein w is the number of fluorine atoms in one mole of starting material. By employing the composite of the invention, the fluorinated alkane is substantially free from corrosion by-products. Examples of fluorinated alkanes which can be produced by the process are hydrofluorocarbons (HFC's), such as HFC 125, and hydrochlorofluorocarbons (HCFC's) such as HCFC 122, 123, 123a, 124, 124a, 133a, among others.

The fluorination process is typically performed under substantially anhydrous conditions, and produces a super acid environment. Anhydrous or substantially anhydrous conditions means that water, which is generally detrimental to the reaction, should be excluded as much as is expediently possible from the reaction zone. HF, which is commercially available, can be supplied directly to the reaction. The halogenated alkenes and alkanes, and the catalysts typically also contain little or no water, and can similarly be supplied directly, e.g., exclusion of moisture from the reaction vessel by means such as a moisture trap is a routine procedure and is well known in the art. After having introduced and mixed the HF and catalyst, a super acid environment can be created. Such super acid environments are typically stronger than 100% sulfuric acid. As a result, super acidity is measured on the $H_o$ scale which in accordance with the present invention, can range from about $H_o$-10 to at least about 30. The corrosion resistant surface of the composites of the invention are capable of withstanding such a super acid environment substantially without releasing corrosion by-products which poison or deactivate the catalyst. By avoiding release of corrosion by-products, the invention is capable of markedly increasing the useful life of the fluorination catalyst.

The fluorination reaction, and attendant formation of a super acid environment, can be carried out batchwise or in a continuous manner in a liquid or vapor phase. Pressure is not critical for practicing the fluorination process. Atmospheric and autogenous pressures are the most convenient.

The contents of the vessel are raised to the appropriate reaction temperature and can be agitated by shaking or stirring for a length of time sufficient to cause occurrence of the reaction. The reaction times can range from about 1 to 17 hours; the typical reaction times are from about 1 to 6 hours.

The catalytic reaction between HF and the halogenated starting material, may create a super acid environment, and may be initiated in the presence of a diluent that may comprise a high-boiling inert liquid, e.g., a perfluorinated ether, or the desired reaction product itself, for example, HCFC-123 in the process for the manufacture of HCFC-123.

Before initiating the catalytic reaction of HF with the halogenated starting material, a metal halide catalyst comprising, for example, a pentachloride may be converted to a pentafluoride by treating the pentachloride with HF and removing the hydrogen chloride by-product.

The design or structural characteristics of the equipment which is used for performing the fluorination process is not a critical aspect of the invention. Equipment having any suitable conventional design, which incorporates the corrosion resistant composites discussed herein and possesses an acceptable thermal conductivity, may be used for manufacturing the fluorinated alkanes. For example, should the fluorination process be conducted at a temperature either below about the boiling point of hydrogen fluoride or below the boiling point of the most volatile reactant, the reaction vessel can be closed or open to the atmosphere provided that moisture is substantially excluded. For a fluorination reaction at or above about the boiling point of hydrogen fluoride or the most volatile component, a closed vessel or a pressure-regulated partially open reactor is used to minimize the loss of reactants.

Regardless of the reactor design, the thermal conductivity of the composite, which is used to fabricate the reaction vessel, is a key aspect of the invention. The wall of the vessel, which is fabricated from an explosively bonded composite, typically ranges from about ¼ to about 2 inches thick, and may possess a thermal conductivity of about 28.7 w/mK to about 37.2 w/mK. It is important to note that thermal conductivity is a function of the composition as well as the thickness of the composite and, accordingly, reactor dimensions and composite compositions are selected to obtain a sufficiently high thermal conductivity. The thermal conductivity must be sufficient to conduct a quantity of heat into the interior of the reactor which is adequate to provide an interior temperature of at least about 180° C. Such a thermal conductivity is important because the heat, which induces the catalytic HCFC and/or HFC formation, is typically supplied from a external source. For example, the reaction vessel can be heated by pipes which encircle the exterior of the reaction vessel, an external jacket welded to the vessel, external electric resistance, among many others. Should the thermal conductivity of the composite which is employed to fabricate the walls of the vessel be too low, the fluorination process is difficult to control and inefficient.

The composite may be shaped or treated in order to fabricate equipment which is to be used for performing the fluorination process discussed above. At least one composite is shaped or treated using conventional metal working processes such as annealing, bending, brazing, hot-rolling, stamping, tempering, welding, among others, in order to assemble the composites into the desired equipment. For example, the composite may be formed or shaped, e.g., by rolling, into parts which are assembled for obtaining a reactor. The shaped composite parts may comprise hemispherical portions, e.g., bottom head, of the wall of a reactor. The vertical portions can be welded together, and the resultant seams therebetween brazed in order to form a unitary structure which defines the walls of the reactor.

Figure 2:
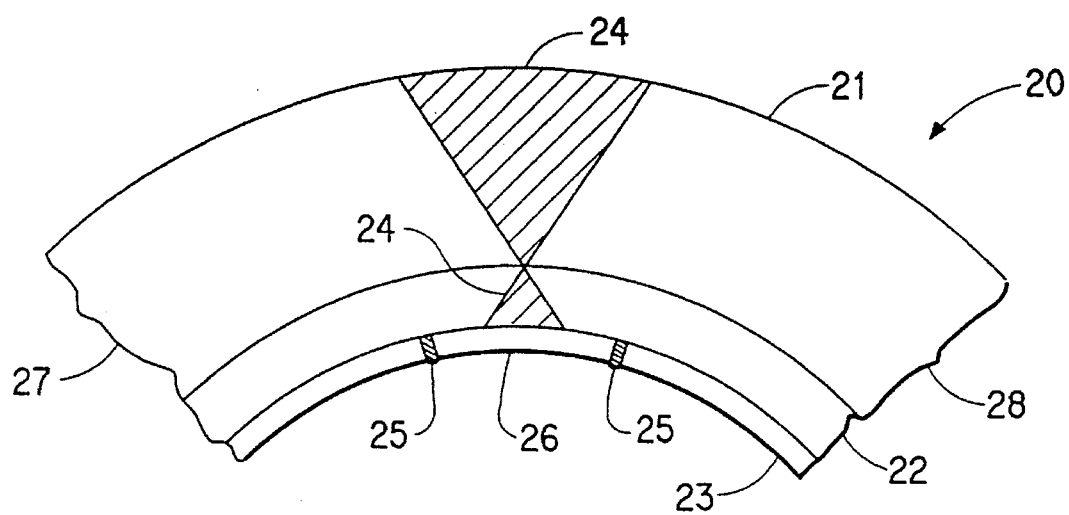
FIG. 2—FIG. 2 is a schematic of a cross-section of another wall of a chemical reactor formed according to the invention.

The configuration of an acceptable reactor wall is illustrated by FIGS. 1 and 2. Referring now to FIGS. 1 and 2, these Figures illustrate a schematic of a cross-section of the wall of a reactor for producing the fluorinated alkenes. FIG. 1 illustrates one embodiment of the wall 10 of a reactor. The wall 10 may comprise an explosively clad composite comprising carbon steel layer 11, Hastelloy C-276 intermediate layer 12, and a layer of corrosion resistant metal 13. When in use, layer 13 of the composite 10 is in direct contact with the fluorination process. In one aspect of this embodiment, layer 13 comprises a 0.02 inch thick gold sheet. The wall 10 is formed by welding together at least two clad hemispherical composites having the desired composition. As illustrated in FIG. 1, clad composite 16 is welded to clad composite 17. The weld is shown in FIG. 1 by the regions labelled as 14. The weld between layers 11 and 12 of clad composites 16 and 17 necessitated forming a cut-out in layer 13. The cut-out was back-filled by brazing to form overlay 15. Overlay 15 protects the seam formed by weld 14 and comprises any brazable material which is highly corrosion resistant. When layer 13 comprises a molybdenum alloy, 24K gold is a preferred brazing material. However, other suitable brazing materials comprise at least one of gold-copper, gold-nickel alloys, among others.

FIG. 2 illustrates an alternative to the embodiment shown in FIG. 1. The wall 20 may comprise an explosively clad composite comprising carbon steel layer 21, Hastelloy C276 intermediate layer 22, and a layer of corrosion resistant metal 23. When in use, layer 23 of the composite is in direct contact with the fluorination process. In one preferred aspect of this embodiment, layer 23 comprises a 0.02 inch thick platinum sheet. The wall 20 is formed by welding together at least two clad vertical composites having the desired composition. To obtain a bottom-head component of a reactor, at least two hemi-spherical composites can be joined together. As illustrated in FIG. 2, clad composite 27 is welded to composite 28. The weld is shown in FIG. 2 by the regions labelled as 24. The weld between layers 22 and 21 necessitated forming a cut-out in layer 23. The cut-out was replaced by brazing into the cut-out a strip 26 of corrosion resistant material. The strip 26 was brazed in two (2) passes using 24K gold wires (0.045 inch diameter wire) labelled as 25 in FIG. 2

In one aspect of the invention the wall illustrated in FIGS. 1 and 2 is characterized by carbon steel base layers, i.e., 11 and 21, which have a thickness which ranges from about 0.75 to about 1.5 inches. The intermediate layers 12 and 22 which may comprise Hastelloy C-276 (ASTM B 575'UNS N10276'), range from about 3/16 to at least ¼ inch in thickness. Corrosion resistant metal layers 13 and 23 have thicknesses which range from 1/32 to at least 1/16 inch. The cut-out region 15 and the insert 26 are approximately 0.75 inch in width and about 0.0625 inch thick.

While particular emphasis in the above discussion has been placed upon manufacturing a fluorinated alkane such as HCFC-123, it is to be understood that the composites of the invention can be used to fabricate reactors or vessels which are used in a virtually unlimited array of processes. For example, such a reactor may be employed to house a hydrodechlorination reaction. Moreover, in some cases at least a portion of the corrosion resistant metal is brazed upon the base metal. For example, a gold alloy sheet, e.g., comprising a eutectic alloy of gold and copper or nickel, may be located between base metal and molybdenum alloy sheets, and brazed together to obtain a composite.

Certain aspects of the invention are illustrated by the following Examples. These Examples demonstrate the desirable corrosion resistance of certain materials which may be exposed to the super acidic alkane manufacturing process.

It is to be understood that the following Examples are provided to illustrate, and not limit the scope of the invention. Unless specified otherwise, the materials which were used in the following Examples are commercially available.

EXAMPLE 1

Corrosion test coupons which measured about 1×½×⅛ inches were exposed in an agitated 20 gallon reactor made of Hastelloy C-276 and containing molten $TaF_5$. A mixture of anhydrous HF and tetrachloroethene (perclene) was fed to the reactor while HCFC-123, HCl and unreacted HF were continuously removed from the reactor to maintain a constant liquid level. The $TaF_5$ concentration was about 17.5%, the HF concentration was about 18%, with about 60% organic and 4.5% HCl. The catalyst was originally charged as approximately 20 pounds of $TaCl_5$, which converts to $TaF_5$ upon the addition of HF, thereby creating a super acid environment. The average rate of perclene feed was about 5.1 pounds/hour. Total exposure hours were 106, of which 100 were with perclene and HF being fed. The temperature during corrosion testing was about 130° C. Corrosion rates for the test coupons were calculated by using the following formula:

Corrosion Rate=(K×delta W) divided by (D×A×T), wherein K is a dimensionless constant, delta W is the loss of weight, D is the density of the corroded material, A is the surface area, and T is the length of exposure to the super acid environment. Corrosion rates (mils per year; thousands of an inch per year) were measured as follows.

| TEST COUPON | |
|---|---|
| MATERIAL | CORROSION RATE |
| Hastelloy B-2* | 4–6 |
| Hastelloy C-276* | 71 |
| Molybdenum | <0.4 |

*Composition of Hastelloy B-2 which was tested corresponded to ASTM B 333 (UNS N10665).
*Composition of Hastelloy C-276 which was tested corresponded to ASTM B 575 (UNS N10276).

EXAMPLE 2

Corrosion tests were carried out substantially in accordance with Example 1, but with the corrosion medium at approximately 40% $TaF_5$, 22.5% HF, 35% organic (85% HCFC-123, 15% HCFC-122), and 2.5% HCl. About 50 pounds of TaCl5 was initially charged to the reactor, and the average rate of perclene feed was about 13.0 pounds/hour. Total exposure hours were about 312; only 250 of which were with perclene and HF being fed. Temperature was about 135° C. Corrosion rates were as follows (mils per year).

| TEST COUPON | |
|---|---|
| MATERIAL | CORROSION RATES |
| Hastelloy B-2 | 15–30 |
| Hastelloy C-276 | 212 |
| Molybdenum | 0.0 |

EXAMPLE 3

Corrosion tests were carried out substantially in accordance with Example 2, but with the corrosion medium at approximately 40% $TaF_5$, 30% HF, 27.5% organic (50% HCFC-123, 50% HCFC-122), and 2.5% HCl. The average rate of perclene feed was 10.7 pounds/hour. Total exposure hours with perclene and HF being fed were about 330. For this and subsequent runs, the corrosion rates are calculated based only on the hours when perclene and HF were being fed, which is when nearly all the corrosion occurs, rather than on total exposure hours. The temperature during corrosion testing was about 130° C. The corrosion rates are as follows (mils per year).

| TEST COUPON | |
|---|---|
| MATERIAL | CORROSION RATES |
| Hastelloy B-2 | 28 |
| Hastelloy C-276 | 131 |
| Molybdenum | 0.1 |
| Gold | 0.2 |
| Palladium | 0.0 |
| Platinum | 0.0 |

EXAMPLE 4

Corrosion tests were carried out substantially in accordance with Example 3, but with an average perclene feed rate of about 10.2 pounds/hour. Total perclene-HF feed hours were about 585. Temperature was about 130° C. Corrosion rates were as follows (mils per year).

| TEST COUPON | |
|---|---|
| MATERIAL | CORROSION RATES |
| Hastelloy B-2 | 10.5–25.4 |
| Hastelloy C-276 | 91.6 |
| Molybdenum (formed via vacuum arc cast) | 0.2–0.6 |
| Molybdenum (formed via powder methallurgy) | 0.2 |
| 59% Molybdenum/41% Rhenium | 0.1 |

EXAMPLE 5

Corrosion tests were carried out substantially in accordance with Example 4, but with a modified agitator which caused higher corrosion. Total perclene-HF feed hours were about 200. Temperature was 130° C. Certain test coupons comprised a material upon which another material had been brazed. Corrosion rates were as follows (mils per year).

| TEST COUPON | |
|---|---|
| MATERIAL | CORROSION RATES |
| Hastelloy B-2 | 9–126 |
| Hastelloy C-276 | 35 |
| 80% Gold/20% Copper eutectic | 0.1 |
| Gold (24 carat) | 0.1 |
| Mo brazed with 80% Gold/20% Copper | 0.7 |
| 95% Molybdenum/5% Rhenium | 0.0 |
| 90% Tungsten/10% Rhenium | 0.0 |
| 95 Mo5Re brazed with 82.5% Gold/17.5% Nickel | 0.4–0.9 |
| Silver | (dissolved) |
| Chromium | (dissolved) |

EXAMPLE 6

Corrosion tests were carried out substantially in accordance with Example 5. Total perclene-HF feed hours were about 362. The temperature during corrosion testing was about 130° C. Corrosion rates were as follows (mils per year).

| TEST COUPON | |
|---|---|
| MATERIAL | CORROSION RATES |
| Hastelloy B-2 | 89–126 |
| Hastelloy C-276 | 153–184 |
| Palladium | 0.2 |
| Copper | (dissolved) |
| Molybdenum (formed via vacuum arc cast) | 0.0 |
| Molybdenum (formed via powder metallurgy) | 0.1 |

EXAMPLE 7

Corrosion tests were carried out substantially in accordance with Example 6. Total perclene-HF feed hours were about 654. The temperature during corrosion testing was about 130° C. Corrosion rates were as follows (mils per year).

| TEST COUPON | |
|---|---|
| MATERIAL | CORROSION RATES |
| Hastelloy B-2 | 15–57 |
| Hastelloy C-276 | 60–128 |
| Mo TZM* | 0.0–1.0 |
| 87% Molybdenum/13% Rhenium | 0.1 |
| 70% Molybdenum/30% Tungsten | 0.0 |

*The composition of the Mo TZM alloy which was tested corresponded to 0.59% Ti, 0.1% Zr, remainder Mo.

EXAMPLE 8

Corrosion tests were carried out substantially in accordance with Example 7, but with the initial amount of $TaCl_5$ increased to about 100 pounds which increased the super acidity of the testing environment. Total perclene-HF feed hours were about 330. The temperature during the corrosion testing was about 130° C. Corrosion rates were as follows (mils per year).

| TEST COUPON | |
|---|---|
| MATERIAL | CORROSION RATES |
| Hastelloy B-2 | 68–627 |
| Hastelloy C-276 | 184–824 |
| 77% Molybdenum/10% Tungsten/13% Rhenium | 0.1 |
| Hexaloy ST* | dissolved |
| Mo TZM | 0.1 |
| 59% Molybdenum/41% Rhenium | 0.1 |
| 95% Molybdenum/5% Rhenium brazed with 80% gold/20% copper | 0.0 |

*Composition comprises SiC without free Si.

EXAMPLE 9

Corrosion tests were carried out substantially in accordance with Example 8. Total perclene-HF feed hours were about 577. The temperature during corrosion testing was about 130° C. Corrosion rates were as follows (mils per year).

| TEST COUPON | |
|---|---|
| MATERIAL | CORROSION RATES |
| Hastelloy B-2 | 14.5–33.7 |
| Hastelloy C-276 | 13.5–17.2 |
| 59% Molybdenum/41% Rhenium | <0.1 |
| 87% Molybdenum/13% Rhenium | <0.1 |
| Gold wire (24 carat) | 0.05 |
| 80% Gold/20% copper wire | 0.2 |
| 95% Molybdenum/5% Rhenium brazed with 80% gold/20% copper | 0.1 |

EXAMPLE 10

Corrosion tests were carried out substantially in accordance with Example 2. Total perclene-HF feed hours were about 930. The temperature during corrosion testing was about 130° C. Corrosion rates were as follows (mils per year).

| TEST COUPON | |
|---|---|
| MATERIAL | CORROSION RATES |
| Hastelloy B-2 | 4.1–14.00 |
| Hastelloy C-276 | 3.9–24.3 |
| 80% Gold/20% copper wire | 0.1 |
| 59% Molybdenum/41% Rhenium | 0.0 |
| 95% Molybdenum/5% Rhenium brazed with 80% gold/20% copper | 0.0 |

What is claimed is:

1. A process for increasing the useful life of a fluorination catalyst comprising:

providing a fluorination reactor which comprises an explosively bonded composite comprising at least one corrosion resistant metal selected from the group consisting of gold, palladium, molybdenum, rhenium, and tungsten, an optional metallic intermediate layer, and a base metal wherein said corrosion resistant metal has a corrosion rate less than about 1 mil/year when exposed to a super acid environment having a $H_o$ which ranges from about −10 to −30 wherein said environment is formed by an interaction between a catalyst and hydrogen fluoride employing said catalyst in said environment, and; increasing the useful life of said catalyst by minimizing release of corrosion by-products from the reactor.

2. The process of claim 1 wherein said catalyst comprises at least one member selected from the group consisting of tantalum pentafluoride, niobium pentafluoride, and antimony pentafluoride.

3. The process of claim 1 wherein the thickness of the composite ranges from about ¼ to 2 inches thick, and said intermediate layer comprises Hastelloy C-276, said metal comprises Mo41Re, wherein said composite has a thermal conductivity of about 28.7 w/mK to about 37.2 w/mK.

4. A process for obtaining a fluorinated alkane comprising contacting at least molar equivalents of at least one starting material selected from the group consisting of (1) at least one halogenated alkene of the formula

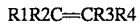

R1R2C=CR3R4 wherein R1, R2, R3 and R4 are individually selected from H, F, and Cl; or (2) at least one chlorinated alkane of the formula

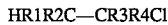

HR1R2C—CR3R4Cl wherein R1 and R2 are individually selected from H and Cl, and wherein R3 and R4 are individually selected from H, Cl, and F, with at least a stoichiometric molar equivalent of HF in the presence of at least one catalyst comprising a trivalent, tetravalent, or pentavalent metal halide wherein the useful life of equipment which is employed to perform said process is increased by fabricating said equipment from at least one explosively bonded composite wherein the composite comprises at least one corrosion resistant metal, an optional metallic intermediate layer, and a base metal, and the corrosion resistant metal has a corrosion rate less than about 1 mil/year when exposed to a super acid environment that has a $H_o$ which ranges from about −10 to −30.

5. The process of claim 1 or 4 wherein the process is operated at a temperature that ranges from about 120° C. to about 200° C.

6. The process of claim 4 wherein the equipment comprises at least one member selected from the group consisting of chemical reactor, agitator, feed pipes, and, internal heating coil.

7. The process of claim 4 wherein the thickness of the composite ranges from about ¼ to 2 inches thick, and said intermediate layer comprises Hastelloy C-276, said metal comprises Mo41Re, wherein said composite has a thermal conductivity of about 28.7 w/mK to about 37.2 w/mK.

* * * * *